United States Patent [19]
Gaffar et al.

[11] 4,430,325
[45] Feb. 7, 1984

[54] TOPICAL TREATMENT OF SKIN LESIONS

[75] Inventors: Abdul Gaffar; Calvin B. Davis, both of Somerset, N.J.

[73] Assignee: Colgate-Palmolive Company, New York, N.Y.

[21] Appl. No.: 333,587

[22] Filed: Dec. 23, 1981

[51] Int. Cl.³ ............................................. A61K 33/42
[52] U.S. Cl. .................................................... 424/128
[58] Field of Search ........................................ 424/128

[56] References Cited

U.S. PATENT DOCUMENTS 4,041,149  8/1977  Gaffar et al. ........................... 424/57

OTHER PUBLICATIONS

Handbook of Non-prescription Drugs, 5th Ed., 1977, pp. 306, 307 & 347.

Primary Examiner—Leonard Schenkman
Attorney, Agent, or Firm—Herbert S. Sylvester; Murray M. Grill; John A. Stemwedel

[57] ABSTRACT

A dermatological composition and method for treating skin lesions employing a peroxydiphosphate salt, such as the tetrapotassium salt, as the essential therapeutically active agent.

3 Claims, No Drawings

TOPICAL TREATMENT OF SKIN LESIONS

This invention relates to topical compositions and methods for the treatment of skin lesions employing a novel and improved compound as the active therapeutic agent.

A great many topical therapeutic agents have been previously proposed for the treatment (alleviation, and/or healing) of skin lesions associated with burns, varicose ulcers, sycosis vulgaris, seborrhea and acne. Illustratively, U.S. Pat. No. 4,126,681 of Nov. 21, 1978 is directed to the use of acetylsalicylic acid (aspirin) as such agent, and U.S. Pat. No. 4,261,982 of Apr. 14, 1981 describes prior art disclosing as such agents various types of zinc salts and antibiotics such as tetracyclin, erythromycin, lindomycin and clindamycin, and proposes the use of zinc and erythromycin combinations and zinc erythromycin compounds.

One of the most widely, if not the most widely, used topical therapeutic agents for treating skin lesions has been benzoyl peroxide. U.S. Pat. No. 4,163,800 of Aug. 7, 1979, in column 1, line 6 to column 2, line 33 discusses skin conditions, diseases and lesions treatable with benzoyl peroxide, its beneficial effects, and the undesirable irritation problems and side effects associated with its use such as excessive drying, heavy scaling, edema, burning, peeling, redness, excessive erythema, allergic contact dermatitis, and sensitization reactions, which discussion is incorporated herein by reference thereto. The latter patent is directed to the reduction of such skin irritation problems by applying the benzoyl peroxide in conjunction with certain guanidine compounds. This expedient of course complicates and increases the cost of manufacturing the preparation, requiring as it does various tests and controls to arrive at selection of the particular guanidine compound, optimum ratios of benzoyl peroxide and guanidine compound, and selection of excipients including vehicles, carriers and/or solvents compatible with both components which, further, are insoluble and must be suspended in water.

There is moreover another highly troublesome problem involved in the preparation, storage and marketing of benzoyl peroxide preparations, namely the sensitivity of the benzoyl peroxide to other conventional ingredients or excipients in the preparation leading to more or less significant degradation of, and loss of oxidizing activity of, the benzoyl peroxide in storage, especially at elevated temperatures. This problem is recognized in the art, as see the article by Bollinger et al entitled "Benzoyl Peroxide Stability in Pharmaceutical Gel Preparations", J. Pharm. Sciences 66 No. 5, May 1977, 718–722. This article describing an investigation "to evaluate various parameters regarding the storage stability of benzoyl peroxide in pharmaceutical gel formulations" ends with the statement "In general, the results of this investigation demonstrated that the stability of benzoyl peroxide in pharmaceutical gel preparations is strongly influenced by the chemical makeup of the formulations and, secondarily, by the storage temperature due to increased reactivity". The benzoyl peroxide functions at least in part by a mechanism involving reaction with and/or decomposition by cysteine in the skin, with liberation of oxygen. Bacterial proteins are thus oxidized, the oxidization thus exerting both antibacterial and comedolytic activity, especially valuable in the treatment of acne and acneiform skin disorders. Degradation of the benzoyl peroxide in storage, i.e. its relatively abbreviated shelf-life, with loss of its ability to release active oxygen, protanto reduces its therapeutic value.

It is an object of this invention to provide compositions and methods for the topical treatment of skin lesions which will not be subject to one or more of the above deficiencies and disadvantages. Other objects and advantages will appear as the description proceeds.

In accordance with certain of its aspects, this invention includes the provision of a dermatological composition for treating skin lesions comprising a safe and therapeutically effective amount of a peroxidiphosphate salt (PDP), especially the tetrapotassium salt (KPDP), and method comprising topically applying such composition to the afflicted situs.

In contrast to benzoyl peroxide compositions, the PDP compositions of this invention are vastly more stable in storage, especially at elevated temperatures, are readily activated by cysteine to liberate active oxygen in situ at the situs of the skin lesion, and produce little or no allergic or irritative skin reactions. The active PDP therapeutic agents in the present compositions are per se substantially more stable in storage than benzoyl peroxide. In U.S. Pat. No. 4,041,149 issued Aug. 9, 1977 to Maria Gaffar, Abdul Gaffar (co-applicant herein) and John Hauschild directed to anti-odor oral compositions containing less than 3 wt.% of PDP as the active anti-odor agent, the preferred KPDP is described as a stable odorless, finely divided, free-flowing, white, non-hygroscopic crystalline solid having a molecular weight of 346.35 and an active oxygen content of 4.6%. It is 47–51% water-soluble at 0°–61° C., but insoluble in common solvents such as acetonitrile, alcohols, ethers, ketones, dimethyl formamide, dimethyl sulfoxide, and the like. A 2% aqueous solution has a pH of about 9.6 and a saturated solution thereof a pH of about 10.9. A 10% solution in water at 25° C. showed no active oxygen loss after four months; and at 50° C. a 10% solution showed an active oxygen loss of 3% in 6 months.

Further, the above-described substantial water-solubility of these PDP agents provide further advantages relative to benzoyl peroxide agents with respect to costs of vehicle and processing, minimization of skin irritation, incompatibilities of components, and the like, in permitting use of water as the sole or major solvent, vehicle or carrier.

Any of the alkali metal, alkaline earth metal, metal or ammonium peroxydiphosphates or their corresponding acid salts that are water-soluble to the extent of about 0.001 weight percent can be used in the compositions of this invention. Examples of these are tetrapotassium peroxydiphosphate ($K_4P_2O_8$), tetralithium peroxydiphosphate ($Li_4P_2O_8$), tetrasodium peroxydiphosphate ($Na_4P_2O_8$), tripotassium monosodium peroxydiphosphate ($K_3NaP_2O_8$), dipotassium disodium peroxydiphosphate ($K_2Na_2P_2O_8$), monopotassium trisodium peroxydiphosphate ($KNa_3P_2O_8$), monopotassium monosodium dihydrogen peroxydiphosphate ($KNaH_2P_2O_8$), trilithium monopotassium peroxydiphosphate ($Li_3KP_2O_8$), dilithium dipotassium peroxydiphosphate ($Li_2K_2P_2O_8$), monolithium tripotassium peroxydiphosphate ($LiK_3P_2O_8$), trilithium monosodium peroxydiphosphate ($Li_3NaP_2O_8$), dilithium disodium peroxydiphosphate ($Li_2Na_2P_2O_8$), monolithium trisodium peroxydiphosphate ($LiNa_3P_2O_8$), monolithium monosodium dihydrogen peroxydiphosphate ($LiNaH_2P_2O_8$), and monolithium monopotassium dihydrogen peroxydiphosphate ($LiKH_2P_2O_8$), in addition to dizinc peroxydiphosphate ($Zn_2P_2O_8$), tetraammonium peroxydiphosphate dihydrate ($(NH_4)_4P_2O_8 2H_2O$), and the acid salts of group 2 metals such as barium dihydrogen peroxydiphosphate ($BaH_2P_2O_8$), calcium dihydrogen peroxydiphosphate ($CaH_2P_2O_8$), and the like.

The compositions of this invention are formulated to contain or comprise a safe and therapeutically effective amount of the essential PDP, preferably KPDP, i.e. an amount sufficient to alleviate skin lesions based on a reasonable benefit/risk ratio normal in any medical treatment, unduly low proportions obviously tending to be insufficiently therapeutic and unduly high proportions obviously tending to introduce skin irritation problems. Typically, these compositions may contain about 8 to about 30 wt.%, preferably about 9 to about 15 wt.%, of the active PDP, in addition to any of the conventional dermatological, toxicologically-and/or pharmaceutically-acceptable excipients, i.e. vehicles, solvents, thickeners, humectants, penetrants, surfactants, chelating agents, emollients, fragrances, colors, preservatives, propellants and the like suitable for use in contact with the tissues of humans and lower animals without introduction of problems or complications such as undue toxicity, irritation, allergic response and the like commensurate with a reasonable benefit/risk ratio. Compatible non-interfering drugs and medicaments exerting other or similar functions such as antibacterials, antimicrobials, antifungals, anesthetics and the like may also be included to broaden the effectiveness of these compositions in which the PDP exerts antibacterial, keratolytic, pharmacological and other therapeutic functions.

It will of course be understood that the PDP does have a sufficient degree of sensitivity to certain other excipients to warrant care in their selection for maximization of stability in storage and function in use. Although other excipients may be employed, the following are recommended as being relatively less likely to be incompatible, reactive or otherwise interfering with the PDP and/or its desired activity in these compositions.

One or a mixture of thickeners may be included, preferably in proportions of about 0.5 to about 10, more preferably about 1 to about 7, wt.% of the composition. A preferred thickener is synthetic hectorite, a synthetic colloidal magnesium alkali metal silicate complex clay available for example as Laponite (e.g. CP, SP, 2002, D) marketed by Laporte Industries Limited. Laponite D analysis shows, approximately by weight, 58.00% $SiO_2$, 25.40% MgO, 3.05% $Na_2O$, 0.98% $Li_2O$, and some water and trace metals. Its true specific gravity is 2.53 and it has an apparent bulk density (g./ml. at 8% moisture) of 1.0.

Other preferred thickeners are hydroxybutyl methyl cellulose, more preferred hydroxypropyl methyl cellulose, and still more preferred hydroxyethyl cellulose (e.g. available as Natrosol).

Still other preferred thickeners are poly(methylvinyl ether/maleic anhydride), available for example as Gantrez AN 139 (GAF Corporation), and colloidal silica thickener available as finely ground Syloid (e.g. 244).

Carboxyvinyl polymer, still another preferred thickener, is for example available as Carbopol (e.g. 934, 940, 941). These products of B. F. Goodrich Co. are described in U.S. Pat. No. 2,798,053, 2,923,692 and 2,980,655, being essentially colloidally water-soluble acidic carboxylic polymers of acrylic acid cross-linked with about 0.75 to about 2.0% of a cross-linking agent of polyallyl sucrose or polyallyl pentaerythritol.

One or a mixture of humectants may be included, preferably in proportions of about 5 to about 45, preferably about 8 to about 25, wt.%. The humectant, preferably propylene glycol and more preferably polyethylene glycol (e.g. PEG 400,600), prevents drying out of the composition and often also functions as a liquid carrier or vehicle, alone or in combination with water.

These compositions may have a pH measured as a 20% aqueous slurry of about 4.5 to about 10.5, but a range of about 7.5 to 10.5, especially about 8.5 to 10.5, is preferred since the PDP, especially KPDP, appears to be more stable, i.e. with better rentention of active oxygen activity, at these more alkaline ranges. The pH can be controlled by inclusion of the required amounts of acidic substances such as citric or benzoic acid, basic substances such as sodium hydroxide, and/or buffering agents such as sodium citrate, benzoate, bicarbonate or carbonate, disodium hydrogen phosphate, sodium dihydrogen phosphate, or mixtures thereof.

The compositions of this invention may contain a non-soap synthetic sufficiently water soluble organic anionic, nonionic or cationic surfactant in concentrations generally ranging from about 0.05 to about 10, preferably about 0.5 to about 5, weight percent, to promote emulsifying and wetting properties. U.S. Pat. No. 4,041,149 discloses such suitable anionic surfactants in col. 4, lines 31–68 and such suitable nonionic surfactants in col. 8, lines 30–68 and col. 9, lines 1–12, which passages are incorporated herein by reference thereto. Pluronic type nonionic surfactants (polyoxyethylene polyoxypropylene block polymers) such as Pluronic F108 and F127 may also be employed. Cationic surfactants are also well known, such as stearyl dimethyl ammonium chloride, other quaternary ammonium, pyridinium and morpholinium halides and sulfates and the like including antibacterial agents such as benzethonium chloride and cetyl pyridinium chloride.

As indicated above, other known non-interfering excipients, drugs and medicaments may be included as desired or required in any particular instance.

Chelating agents such as EDTA (disodium ethylenediamine tetraacetate) and nitrilotriacetate may be included, preferably in proportions of about 0.01 to about 1 wt.% to inhibit decomposition of the PDP by metal ions.

The compositions of this invention may be provided in any convenient, preferably fluid, form such as pastes, creams, gels, aerosols, solutions or dispersions, and applied topically to the afflicted situs, i.e. the skin lesion and immediately surrounding area, by any suitable means such as by manual spreading or rubbing, applicator pads, or brushes, aerosol spray, pump spray or the like. The dose range, rate and duration of treatment will of course vary with and depend upon the type and severity of the skin disorder, the area of the body which is afflicted, patient response and like factors within the knowledge and judgment of the user or attending physician. A typical usage rate is about 0.001 g/cm.$^2$ to about 0.1 g/cm.$^2$ of skin per application, one or more times daily for up to a week or more to promote healing and relieve dermatoses.

Skin lesions treatable by the compositions of this invention may include macules, patches, papules, plaques, nodules, comedones, burns, varicose and other skin ulcers, seborrhea, sycosis vulgaris, pustules, cysts and the like accompanying or produced by such skin afflictions of bacterial origin or otherwise such as impetigo contagioso or ecthyma, bullous impetigo, dermatitis exfoliative, erysipelas, folliculitis, hidradenitis suppurativa, paronychial infections, erythrasma, seborrhea and especially common acne and acne vulgaris in all forms.

In preparing the compositions of this invention, the components may be thoroughly blended with each other in any order. The preferred aqueous compositions, i.e. those containing at least 10, preferably at least 30, more preferably at least 50, wt.% of water, are most advantageously prepared by dissolving the PDP in some or all the (preferably chelated) water and blending the resulting solution with a mixture of the remaining ingredients. Solubilizing the PDP in water is in fact preferred even when a composition containing less than 5 wt.% of water is being prepared, since the solution can then be more quickly and homogeneously blended with the other ingredients.

The following examples are further illustrative of the nature of the present invention and are not to be regarded as limitative. All amounts and proportions referred to herein and in the appended claims are by weight unless otherwise indicated.

In the following Table I, the stability of the KPDP is evaluated by monitoring active oxygen (A.O.) contents by the following procedure:

KPDP readily hydrolyzes in an acid medium as follows:

$$P_2O_8^{-4} + 2H_2O \rightarrow 2HPO_4^{-2} + H_2O_2$$

An excess of ferrous ammonium sulfate is added to reduce peroxide:

$$2Fe(NH_4)_2(SO_4)_2 + H_2O_2 + H_2SO_4 \rightarrow Fe_2(SO_4)_3 + 2(NH_4)_2SO_4 + 2H_2O$$

The excess of ferrous ion is back titrated with ceric sulfate:

$$2Fe(NH_4)_2(SO_4)_2 + 2Ce(SO_4)_2 \rightarrow Ce_2(SO_4)_3 + Fe_2(SO_4)_3 + 2(NH_4)_2SO_4$$

The A.O. is found by difference.

TABLE I

| | Example (Wt. %) | |
|---|---|---|
| | 1 | 2 |
| Gantrez AN-139 | 2.2 | — |
| Laponite 2002 | — | 5.0 |
| PEG 600 | 10.2 | 10.0 |
| Pluronic F108 | 3.0 | 3.0 |
| KPDP | 10.0 | 10.0 |
| EDTA | 0.1 | 0.1 |
| Water - q.s. to 100 | Active Oxygen (A.O.) | |
| Theoretical | 0.442 | 0.442 |
| Initial at RT (75° F.) | 0.439 | 0.435 |
| Aged 3 weeks at RT | 0.425 | 0.438 |
| Aged 7 weeks at RT | 0.425 | 0.407 |
| Aged 3 weeks at 100° F. | 0.427 | 0.431 |
| Aged 7 weeks at 100° F. | 0.427 | 0.429 |
| Aged 3 weeks at 120° F. | 0.357 | 0.419 |
| Aged 7 weeks at 120° F. | 0.357 | 0.415 |

Considering the uncertainty of the determination of active oxygen ($-10\%$, that is, the method underestimates the A.O. by 10%), the above formulations show good A.O. stability at 100° F. for 3 weeks (equivalent to a 1 year shelf life) and 7 weeks (equivalent to a shelf life of at least 2 years). The formulation of Example 2, in fact shows reasonably good A.O. stability at 120° F. for 7 weeks (equivalent to a shelf life much longer than 2 years). These formulations in the form of creams are prepared by solubilizing the KPDP in water and blending the solution with a mixture of the other ingredients. The creams are applied topically to acne lesions at about 0.05 g/cm.$^2$ of skin twice daily for 2 weeks.

This invention has been disclosed with respect to preferred embodiments, and various modifications and variations thereof obvious to those skilled in the art are intended to be included within the spirit and purview of this application and the scope of the appended claims.

We claim:

1. The method of treating skin lesions comprising topically applying a dermatological composition comprising a safe and therapeutically effective amount of a peroxydiphosphate salt to the afflicted situs.

2. The method according to claim 1 wherein said salt is a tetrapotassium peroxydiphosphate.

3. The method according to claim 2 wherein the composition contains at least about 8 wt.% of said salt.

* * * * *